United States Patent [19]

Christensen

[11] Patent Number: 5,233,662
[45] Date of Patent: Aug. 3, 1993

[54] ORAL CONTROLLER METHOD AND APPARATUS

[76] Inventor: Chris S. Christensen, 3938 SW. Fir Grove Rd., Wilsonville, Oreg. 97070

[21] Appl. No.: 787,896

[22] Filed: Nov. 5, 1991

[51] Int. Cl.$^5$ .............................................. A61F 1/20
[52] U.S. Cl. ...................................... 387/70; 341/21; 340/825.19; 340/407
[58] Field of Search ........................... 381/70; 341/21; 340/825.19, 407

[56] References Cited

U.S. PATENT DOCUMENTS

| | | |
|---|---|---|
| 3,241,115 | 3/1966 | Maling . |
| 4,207,959 | 6/1980 | Youdin et al. . |
| 4,408,192 | 10/1983 | Ward et al. . |
| 4,486,630 | 12/1983 | Fetchko . |
| 4,605,927 | 8/1986 | Katz et al. . |
| 4,641,292 | 2/1987 | Tunnell et al. . |
| 4,728,812 | 3/1988 | Sheriff et al. ........... 340/825.19 |
| 4,746,913 | 5/1988 | Volta . |
| 4,758,829 | 7/1988 | Smith, III . |
| 4,783,656 | 11/1988 | Katz et al. . |
| 4,989,253 | 1/1991 | Liang et al. . |

FOREIGN PATENT DOCUMENTS 2395559 2/1979 France ............................ 340/825.19

OTHER PUBLICATIONS

IBM Technical Disclosure Bulletin, vol. 32, No. 4B, Sep., 1989, pp. 10-13.

Primary Examiner—Forester W. Isen
Attorney, Agent, or Firm—Kolisch Hartwell Dickinson McCormack & Heuser

[57] ABSTRACT

An oral controller and related method for lingual control of remote apparatus are disclosed. Preferably, the controller includes a mouthpiece having an intraoral structure and lingual transducer electronics including an array of photosensitive switches the light beams of which are selectively temporarily interruptible by the placement of the user's tongue in a light beam's path. A normally open electrical contact switch and associated circuitry including one or more batteries are provided for detecting closure of this switch when the mouthpiece is properly placed in the user's mouth, at which time controller circuitry within a separate housing is activated and the photosensitive switches are operated at a low, battery-saving duty cycle. Openings of the photosensitive switches are detected, and their sequence encoded and transmitted, e.g. in the form of an audio signal or a luminous, ultrasonic or RF (modulated) carrier signal, to a remote wireless receiver capable of decoding the lingual placement sequences into symbolic control codes, e.g. computer commands. Preferably, the transmitter or receiver produces an audible tone representing the control code to provide aural feedback to the user. In a proposed modification to the invention, all switch, transducer and transmitter circuitry, including the battery or batteries, are housed in a modified mouthpiece structure the weight of which is partly supported by the user's chin.

11 Claims, 3 Drawing Sheets

FIG.7

ORAL CONTROLLER METHOD AND APPARATUS

BACKGROUND AND SUMMARY OF THE INVENTION

This invention relates generally to controllers operated by selective lingual placement. More particularly, it concerns lingual transducers and oral controllers providing intraoral photosensitive switch arrays the light beams of which are interruptible by selective tongue placement to signal, thus to control, a remote device such as a computer, and a related method.

Prior art oral controllers require the user to complete a circuit with the tongue to provide binary, or on/off, control of an external device. The problems with such controllers include their size and power requirements that render long-term, uninterrupted use uncomfortable if not impossible. The simplistic coding schema used with such prior art controllers greatly limit their versatility as general purpose controllers useful, for example, in the operation of a computer without tying the user's hands. It is also seen that real-time feedback to the users of such controllers as to the accuracy of their lingual placement is not emphasized. The use of electrically energized metallic contacts within a user's mouth can cause a mild electrical shock or tingling sensation and can leave a bitter taste.

As is evident from the plethora of languages and dialects having the subtlest of nuance, lingual control can be developed to a high degree in terms of repeatable shaping, moving and placing accuracy. Yet there have been no oral controllers that facilitate lingual control of complex apparatus without so discomforting their users so as to discourage use of such controllers.

Accordingly, it is a principal object of the present invention to provide a versatile oral controller of complex external apparatus such as a computer.

It is also an important object of the invention to provide such a controller that is safe, comfortable and easy to use.

Another object is to provide an oral controller that draws little power in normal operation whether in use or not, thereby to render it compact and lightweight.

Yet another object of the invention is to provide a lingual transducer that relies on photosensitive switch arrays and selective lingual placement in the path of light beams for control thereof.

One other object is to provide such a controller with a coding scheme used in communication between a local transmitter and a remote receiver that provides a powerful and broad lingual vocabulary.

An equally important object is to provide the user of such a controller with audio feedback to assist in accurate tongue placement.

It is of course an object of the invention to provide such a controller that is easy to manufacture and cost-effective.

In very brief summary of the invention in its preferred embodiment, an oral controller having an at least partly intraoral lingual transducer portion including photosensitive switch detection and power supply circuitry; and having optionally an encoding and transmitting circuitry portion is provided. Low battery drain is made possible by supplying power to the controller circuitry and photosensitive switch array only upon the detected closure of a normally open switch on the mouthpiece which is closed when the mouthpiece is properly placed in the user's mouth, and by energizing the photosensitive switches only periodically at a low duty cycle. A versatile coding scheme potentially having nearly forty symbols or command elements is provided, and such selected codes are used to modulate an infrared carrier for transmission to a remote wireless receiver. A receiver decodes the coded symbols and provides for the control, for example, of relatively complex apparatus such as a computer. Preferably, an audible signal stream is generated by the transmitter as feedback to assist the user in accurate tongue placement and linguistic development.

These and other objects and advantages of the invention will become more readily apparent by reading the following description and by referring to the accompanying drawings.

DETAILED DESCRIPTION OF THE PREFERRED EMBODIMENT

Figures 1, 2:
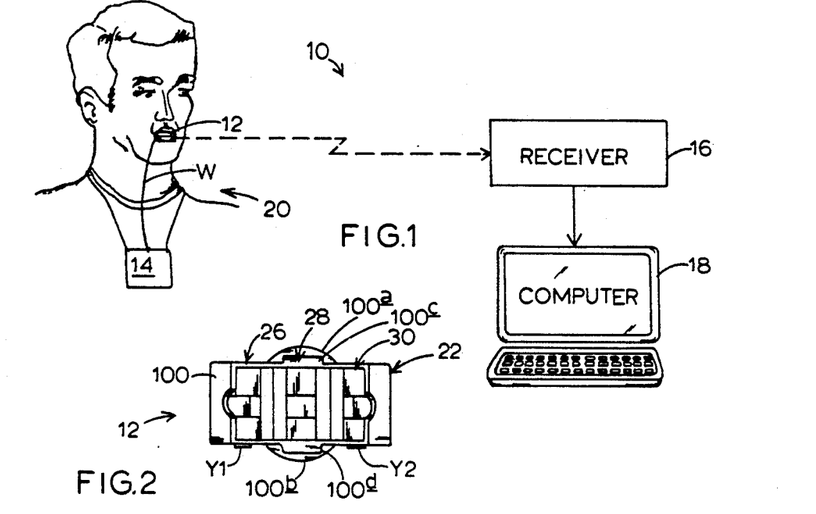
FIG. 1 is a schematic system block diagram of the oral controller of the invention made in accordance with its preferred embodiment.
FIG. 2 is a rear elevation of a mouthpiece that forms a part of the controller illustrated in FIG. 1.

Referring first to FIG. 1, an oral controller made in accordance with the preferred embodiment of the invention is indicated generally at 10. Controller 10 comprises a mouthpiece 12 including a lingual transducer and associated switch and signal conditioning circuitry to be described, a transmitter 14 including an encoder preferably housed separately from mouthpiece 12 but operatively connected thereto and a wirelessly remote receiver 16 responsive to transmitter 14 including a decoder. Mouthpiece 12 includes plural photosensitive switches operable by the user's selective tongue placement proximately or remotely to control a device such as a computer 18.

Mouthpiece 12 is a compact, lightweight structure that easily can be held in the user's mouth between the user's lips and teeth, as indicated in FIG. 1. An intraoral structure or region thereof includes plural, normally closed, so-called 'slotted' photosensitive switches the photocoupling light beams of which can be momentarily interrupted selectively by lingual placement in one of the beams' paths. The actuation of one of the photosensitive switches produces a change of state in a signal that is conditioned by circuitry within mouthpiece 12 and routed via a plural conductor cable or wire harness W to transmitter 14 located within a separate housing that preferably is worn around the user's neck on a cord or necklace.

Transmitter 14, which is operatively coupled with the photosensitive switches, detects the user-selected actuation (opening) of each and every one thereof, ad encodes its occurrence as data by generating a coded signal or signal stream indicative thereof. Transmitter 14 modulates an audio or luminous carrier with the data in accordance with a defined coding scheme for transmission or communication of the switch closure sequence data to a remote receiver. The data-modulated carrier drives a speaker or one or more infrared light emitting diodes (IREDs) located in mouthpiece 12 to produce a data encoded audio or luminous carrier signal detectable by remote receiver 16. By placing his or her tongue proximate photosensitive switches 26, 28, 30 in accordance with the predefined closure sequence or coding scheme, which as will be seen is quite versatile, the user is able to remotely control even a general purpose device such as computer 18.

Figure 6:
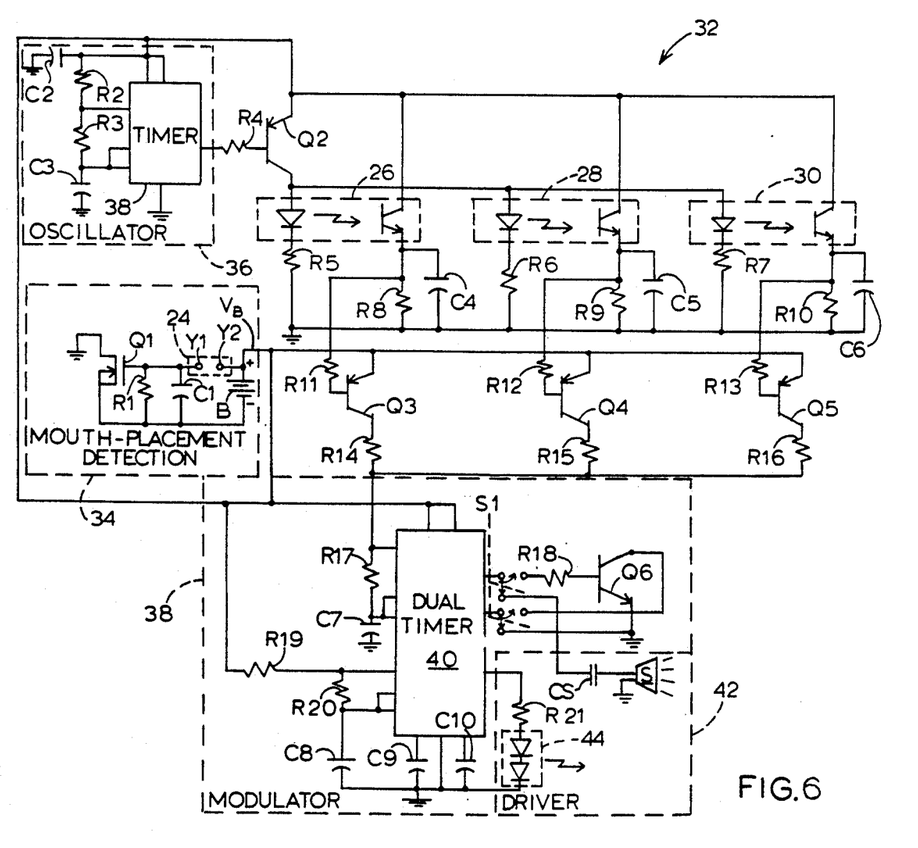
FIG. 6 is a detailed circuit diagram of the transmitter portion of the system of FIG. 1.

Turning briefly to FIGS. 2 and 6, mouthpiece 12 is seen preferably to form a part of what will be referred to as a lingual transducer 20 comprising an intraoral structure 22 including a normally open electrical switch 24 having spaced electrical contacts Y1, Y2, with contacts Y1, Y2 being located on the outside of structure 22 in a location where they can be bridged, thus enabling switch 24 to be closed by conduction therebetween by the user's skin when structure 22 is placed in the mouth. Intraoral structure or region 22 also includes at least one, and preferably three or more, photosensitive so-called "slotted" switches such as switches 26, 28, 30 having light beam-coupleable terminals supplied with a battery voltage $V_B$ upon closure of normally open switch 24. Switches 26, 28, 30 thereafter are normally closed by such a light beam and are actuable (openable) by selective placement of the user's tongue proximate the switches, e.g. lingual placement in the path of one such beam at a time, thereby momentarily to interrupt the same and to open the corresponding one of photosensitive switches 26, 28, 30.

Lingual transducer 20 also includes transducer electronics 32 coupleable with intraoral structure 22 for detecting closure of normally open switch 24, for supplying thereupon voltage $V_B$ to photosensitive switches 26, 28, 30, for detecting actuation of one thereof and for generating a signal indicative of such lingual placement in the corresponding light beam's path. Thus, normally open electrical switch 24 and an associated portion of transducer electronics 32 perform the function in oral controller 10 of a mouth-placement detection circuit 34 coupled with mouthpiece 12 for applying power to photosensitive switches 26, 28, 30 upon detection that mouthpiece 12 is in contact with the user's mouth.

Referring still to FIGS. 2 and 6, a preferred embodiment of the invention is illustrated wherein transmitter 14 generates a coded signal or signal stream that takes the form of a data-modulated, frequency-shift keyed (FSK) sonic (audible) signal or infrared (inaudible and invisible) modulated carrier signal. For the sake of brevity, these respectively preferred and alternative embodiments are indicated schematically by way of a double-pole, double-throw (DPDT) switch S1 in FIG. 6, which switch represents logically, and not necessarily physically, selection of the alternative coded outputs of transmitter 14. It will be understood that preferably one or the other, but perhaps not both, of the infrared or audio signal output circuits might be implemented in a particular embodiment of the invention in order to achieve desired compactness and lightness in oral controller 10.

An audible output signal is believed to be particularly advantageous in that it provides aural feedback aiding accurate lingual placement by the user proximate photosensitive switches 26, 28, 30, whether in training or normal use of lingual transducer 20 alone or as a part of oral controller 10. Accordingly, a preferred embodiment of the invention would incorporate the audio output circuit shown in FIG. 6 (without switch S1 and the alternative infrared output circuit) as a part of transmitter 14, or, alternatively, as a part of receiver 16 (which embodiment would provide a positive indication also that the communication link between the transmitter and receiver is operative). As will be seen, at least one of two illustrated input circuits to receiver 16 would be provided in correspondence with the signal output by driver 42 of transmitter 14.

Figure 7:
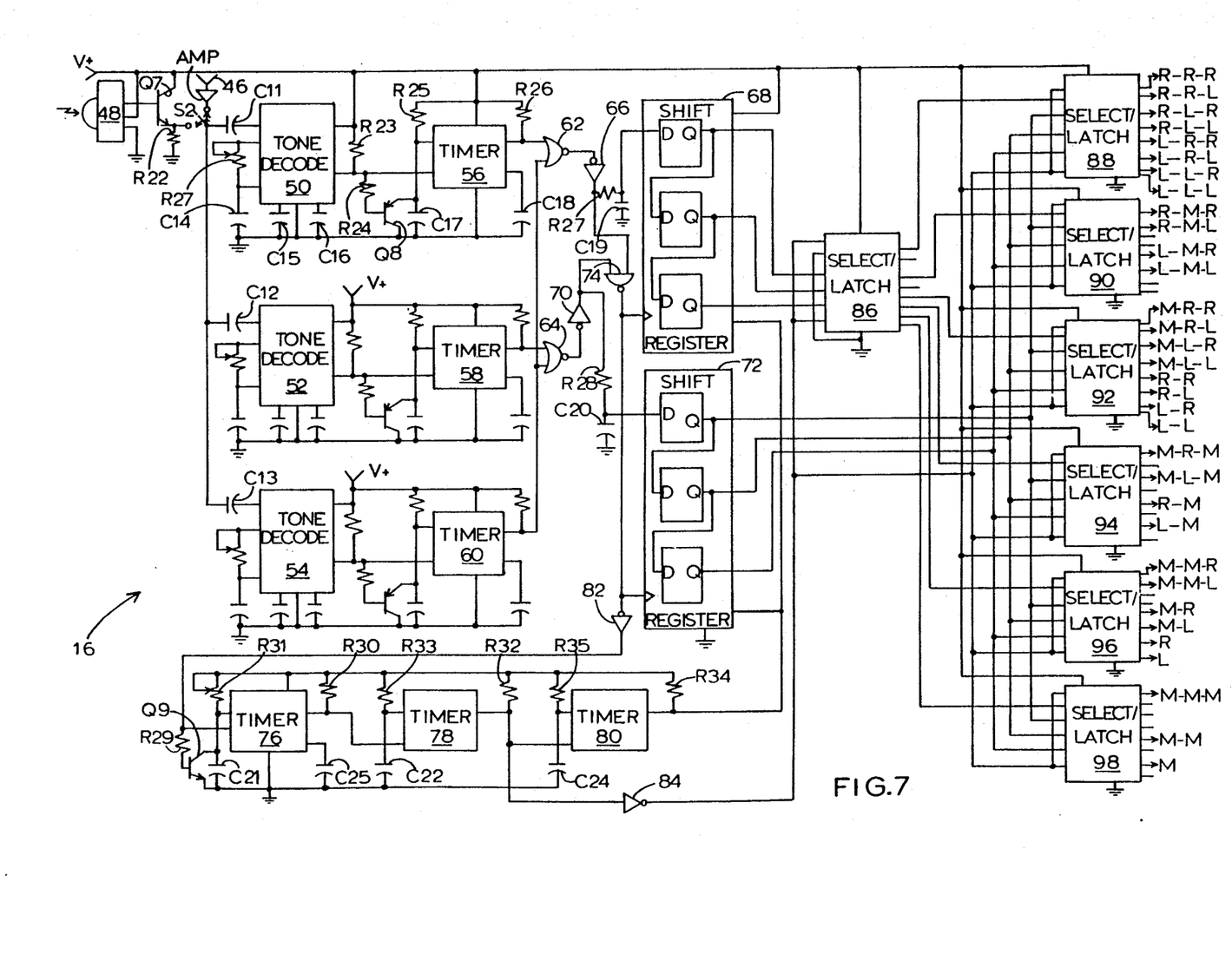
FIG. 7 is a detailed circuit diagram of the receiver portion of the system of FIG. 1.

Turning briefly now to FIGS. 1 and 7, receiver 16 will be described in some detail. Receiver 16 is responsive to the signal stream generated by transmitter 14, and decodes the signal stream into one or more coded symbols for controlling a device, e.g. computer 18, that is typically remote from, but may proximate to, the user. As is pointed out above in reference to transmitter 14, such controlling of computer 18 by the decoding of the signal stream into one or more coded symbols is effected by the user's selective operation of mouthpiece 12 switches 26, 28, 30 in accordance with what will be referred to herein as a control 'language' having a predetermined 'vocabulary' or command repertoire. This language will be described in more detail by detailed reference to FIG. 7.

As suggested above by reference to transmitter 14, receiver 16 may be equipped with either an audio signal input circuit or a luminance signal input circuit, as represented schematically by switch S2. Again, it will be appreciated that, in practice, one or the other, but typically not both, of the input circuits would be implemented, with the selection with respect to transmitter 14 corresponding to the selection made with respect to receiver 16.

Those skilled in the art will appreciate that transmitter 14 may be implemented with both the audio and the luminance signal output circuits, precisely as illustrated in FIG. 6, whereby transmitter 14 is made to generate either an audio or a luminance signal by the positioning of a physical switch S1 or, for example, a jumper wire or printed circuit board (PCB) trace. Complementarily, receiver 16 may be implemented with both the audio and the luminance signal input circuits, precisely as illustrated in FIG. 7, whereby receiver 16 is made to respond to either an audio or a luminance signal by the positioning of a physical switch S2 or such a jumper wire. This would render transmitter 14 and receiver 16 more versatile, in that it would provide the added advantage of making the audio or luminance operation of apparatus 10 user selectable. Finally, those skilled in the art will appreciate that, within the spirit of the invention, transmitter 14 and receiver 16 might be implemented (with the addition, for example, of appropriate contention-avoidance circuitry) such that audio and luminance carriers simultaneously are transmitted and received, thereby providing redundancy in the communication of lingually coded data to the remote device.

Referring in more detail to FIGS. 1, 2 and 6, mouth-placement detection circuit 34 may be seen to include dual contacts Y1, Y2 of normally open switch 24 located on the exterior of mouthpiece 12 in a region where, when mouthpiece 12 is positioned normally in a user's mouth, the user's lower lip touches contacts Y1, Y2. In such position, the relatively low skin resistance of the user's lips (which resistance typically is lowered even further by the natural inclination of users to lick their lips) provides a conductive path between contacts Y1, Y2 and closes normally open switch 24 (refer to FIG. 6).

Mouth-placement detection circuit 34 may be seen also preferably to include a battery B (preferably between approximately 4.5 and 6 volts), metal-oxide semiconductor, field-effect transistor (MOSFET) Q1, a 10-M$\Omega$ bleed resistor R1 and a 0.47-$\mu$F storage capacitor C1. Preferably, only during such lip contact as is described above does DC power from battery $V_B$ reach those portions of transducer electronics 32 that are not involved in mouth-placement detection. Such powering of the remainder of the circuitry occurs by supplying $V_B$ between the gate and drain of MOSFET Q1 (causing it to conduct and thus effectively to ground the negative terminal of battery B), $V_B$ being suitably held up to prevent inadvertent, momentary power loss by capacitor C1. With apparatus 10 not in use, i.e. when contacts Y1, Y2 are not closed by proper lip contact thereon, resistor R1 discharges capacitor C1. MOSFET Q1 is thereby turned off, opening the circuit between the negative terminal of battery B and circuit ground. Thus, the life expectancy of battery B is greatly extended.

Transducer electronics 32 may be seen to include, in addition to photo-sensitive switches 26, 28, 30 and mouth-placement detection circuit 34, an oscillator circuit 36 for producing a square-wave, or periodic pulse stream, digital signal of predetermined frequency and duty cycle. Oscillator circuit 36 preferably includes a timer circuit 38 of any suitable type connected with external precision resistors and capacitors, e.g. resistors R2, R3, capacitors C2, C3, in accordance with timing formulae specified by the particular circuit's manufacturer. The square-wave (or periodic pulse stream) output signal from oscillator circuit 36, which in accordance with the preferred embodiment of the invention is an approximately 20-% duty cycle, 80-Hz signal, drives via a 10-k$\Omega$ resistor R4 the base of a PNP transistor Q2. Thus, preferably photosensitive switches 26, 28, 30 are energized, in accordance with the preferred embodiment of the invention, only periodically at a predetermined, relatively low duty cycle, e.g. they are energized only approximately one-fifth of the time that mouthpiece 12 is positioned within the user's mouth in contact with electrical switch 24. Despite the constant supply of power to certain other circuit elements, this one-fifth duty cycle on switches 26, 28, 30 reduces the net current draw on battery B by approximately two-thirds, thereby further preserving power and further extending the life of battery B by at least a factor of three.

The emitter of transistor Q2 is biased to approximately the voltage level of the battery $V_B$ (when switch 24 is closed), and the collector of transistor Q2 is connected in parallel to first drive terminals (on the light-emitting diode (LED) side) of switches 26, 28, 30. First sense terminals (on the light-responsive transistor side) of switches 26, 28, 30 are connected to $V_B$, as shown in FIG. 6. The other drive terminals of switches 26, 28, 30 are connected through 220-$\Omega$ resistors R5, R6, R7 to a common ground. The other sense terminals of switches 26, 28, 30 are connected via the parallel combination of 330-k$\Omega$ resistors R8, R9, R10 and 0.47-$\mu$F capacitors C4, C5, C6 to ground. The other sense terminals of switches 26, 28, 30, which are connected with the resistor/capacitor parallel combinations, are connected also via 10-k$\Omega$ resistors R11, R12, R13 to the bases of PNP transistors Q3, Q4, Q5, the emitters of which are connected to $V_B$.

The collectors of transistors Q3, Q4, Q5 are connected via disparately valued resistors R14 (preferably 150-k$\Omega$), R15 (preferably 68-k$\Omega$), R16 (preferably 22k$\Omega$) together as a singular input to a modulator circuit 40. Upon the opening of one of photosensitive switches 26, 28, 30, e.g. by the placement of the user's tongue between the contacts of one of switches 26, 28, 30 momentarily (e.g. typically a few hundred milliseconds) to interrupt the light beam oscillating on and off therebetween, the corresponding one of transistors Q3, Q4, Q5 turns on and effectively connects the corresponding one of resistors R14, R15, R16, along with $V_B$ to which it is connected, into a first timer 40a of dual timer circuit 40 of modulator 38. Essentially, the resistor corresponding with the user-selected one of photosensitive switches 26, 28, 30 is then connected with the gate input to timer 40a, along with a fixed 68-k$\Omega$ resistor R17 and a 0.01-$\mu$F capacitor C7 connected therewith as shown, to determine the frequency with which first timer 40a oscillates.

Resistor values R14, R15 and R16 are chosen, relative to the value of resistor R17, to produce three distinct modulation frequencies. In accordance with the preferred embodiment, these frequencies are set by R14, R15 and R16 at approximately 500-Hz, 700-Hz and 900-Hz, respectively. In the event of tongue placement in proximity to one of the photosensitive switches, the output of first timer 40a thus is a square wave of a corresponding one of three frequencies sufficiently frequency separated that they can be distinguished from one another by receiver 16. An NPN transistor Q6 connected to the output of first timer 40a via a 100-k$\Omega$ resistor R18 inverts this square wave output and enables operation of a second timer 40a of dual timer 40. Second timer 40b generates a 40-kHz square wave carrier signal that is modulated off and on at the frequency of the output of first timer 40a, e.g. 500-Hz, 700-Hz or 900-Hz. The timing of second timer 40b is set by a 1-k$\Omega$ resistor R19, a 22-k$\Omega$ resistor R20 and a 1000-pF capacitor C8. First and second timers 40a, 40b of dual timer circuit 40 are decoupled by 0.01-$\mu$F capacitors C9, C10.

Referring still to FIG. 6, an output driver circuit 42 includes either a speaker S and associated decoupling capacitor SC (which produce a preferably audible, audio signal) or a 12-$\Omega$ resistor R21 in series with an IRED pair 44 (which produce a preferably infrared luminance signal), or both in which case the position of switch S2 determines whether transmitter 14 operates as an audio or luminance signal transmitter. Those skilled in the art will appreciate that, within the spirit of the invention, transmitter 14 can be implemented by alternative means to exhibit different operational characteristics. For example, photosensitive switches 26, 28, 30 might use visible rather than infrared light and/or might be single-ended (with light source/sensor and opposing reflective mirror) rather than two-ended (with light source and opposing light sensor); amplitude, phase or other modulation schemes of any desired character might be used to communicate to a remote controller data and/or commands indicative of the user's lingual placement; circuit topology and component type and values might be changed.

Turning now to FIG. 7, receiver 16, the circuitry of which is powered by a DC voltage V+ (which may be supplied by a battery, not shown), includes a microphone 46 (indicated schematically as an antenna) of any suitable design for receiving the audio signal output by speaker S of driver 42, and/or an infrared light-responsive receiver/demodulator circuit 48 for receiving and demodulating the 40-kHz luminance signal carrier output by IRED pair 44 of driver 42. It will be appreciated that either one or both of microphone 46 and receiver/demodulator circuit 48 might be implemented in a given embodiment of the invention, and that, in the latter case, the position of switch S2 would determine whether receiver 16 is responsive to audio energy or modulated infrared carrier energy within the frequency band of the signal output by driver 42 of transmitter 14. It also will be appreciated that alternative means of detecting the transmitted energy may be used. For example, if transmitter 14 is an ultrasonic or RF transmitter, then of course receiver 16 would be equipped with an ultrasonic or RF transducer, or other suitable signal-detecting means, at its input.

The output of receiver/demodulator circuit 48 is DC level-set by an NPN transistor Q7 the emitter of which is grounded through a 1-kΩ resistor R22. The output of microphone 46 is DC level-set and conditioned by an amplifier labeled AMP. One or the other of the detected audio or luminance signals is coupled via switch S2 and 0.1-μF capacitors C11, C12, C13 to an input of each of three tone decode (decoder) circuits 50, 52, 54. Tone decode circuits 50, 52, 54 are connected identically with corresponding timer circuits 56, 58, 60 and external fixed and variable resistors and capacitors to be described by reference only to tone decode circuit 50. For example, each tone decode and timer circuit pair, e.g. tone decode circuit 50 and timer circuit 56, preferably is connected as shown to grounded 0.1-μF, 4.7-μF, 2.2-μF, 0.1-μF, 0.1-μF capacitors C14, C15, C16, C17, C18; to fixed 2.2-kΩ, 10-kΩ, 1-MΩ, 2.2-kΩ resistors R23, R24, R25, R26; to a variable 25-kΩ resistor (potentiometer) R27; and to a common collector PNP transistor Q8.

Those of skill in the arts will appreciate that timer circuits 56, 58, 60 are used as 1-shot multivibrators that produce an output signal at the end of a tone from tone decode circuits 50, 52, 54. For example, for the duration of an approximately 500-Hz tone, as decoded by tone decode circuit 50, timer circuit 56 is held off by transistor Q8, but upon the removal of such tone—which of course corresponds with removal of the tongue from proximity with photosensitive switch 26 of mouthpiece 12—timer circuit 56 outputs a signal indicating that such tone was received by receiver 16. It will be understood that the corresponding circuitry associated with tone decode/timer pairs 52/58 and 54/60 preferably comprises components having identical values to those of tone decode/timer pair 50/56 and that such tone decoder/timer pairs operate similarly to tone decode/timer pair 50/56. Of course, the variable resistors associated with tone decode circuits 52, 54 would be set such that they are responsive to tones of different frequencies, e.g. 700-Hz and 900-Hz, respectively.

Thus, each of interconnected decode/timer pair 50/56, 52/58, 54/60 is tunable, by properly setting the corresponding variable resistor, e.g. potentiometer R27, to produce an active digital output signal upon the detection at its input of a signal of one of the three modulating frequencies to which receiver 16 is to respond. For example, tone decode/timer pair 50/56 would be tuned to respond to energy centered in the 500-Hz frequency band, decode/timer pair 52/58 would be tuned to respond to energy centered in the 700-Hz frequency band and decode/timer pair 54/60 would be tuned to respond to energy centered in the 900-Hz band, which frequency bands correspond to the frequencies output by transmitter 14.

The outputs of timers 56, 60 are input to a NOR gate 62, and the outputs of timers 58, 60 are input to a NOR gate 64. The output of NOR gate 62 is inverted by an inverter 66, the output of which drives the gate input to a first, three-bit shift register 68. Similarly, the output of NOR gate 64 is inverted by an inverter 70, the output of which drives the gate input to a second, three-bit shift register 72. The inverted outputs of NOR gates 62, 64 are input also to a NAND gate 74, the output of which is used synchronously to clock into shift registers 68, 72 data that represents the user's sequential plural photosensitive switch actuations. Those skilled in the art will appreciate that 1-kΩ resistors R27, R28 and grounded 100-pF capacitors C19, C20 slightly delay the arrival of the clock input to shift registers 68, 72 in order to provide sufficient gate setup time therebefore.

Referring still to FIG. 7, sequentially connected timer circuits 76, 78, 80 are provided to enforce a photosensitive switch activation timing protocol on the user of apparatus 10. Importantly, photosensitive switches 26, 28, 30 may be sequentially actuated by the user's tongue placement proximate thereto, thereby to effect the coding of a wide variety of controls. For example, the preferred embodiment of the invention permits the user to actuate one, two or three switches in a relatively short, predetermined interval of time, thereby multiplying the user's command repertoire many fold. If the user too slowly actuates the switches in the desired sequence, however, then what the user intended as a triple-switch actuation sequence will be misinterpreted by receiver 16 as a series of three separate, single-switch actuations. For example, if the user intends to actuate, in sequence, the left switch, the middle switch and then the right switch—a sequence that might be described as "L-M-R"—but delays too long, e.g. more than a second, between successive switch actuations, then receiver 16 will interpret the sequence instead as being first an "L", followed by an "M", followed by an "R" three separate signals, or interpretable codes, according to the invented language protocol.

Timer circuit 76 enforces a predetermined maximum interswitch actuation timing protocol on the user. If the user delays too long between successive switch actuations, each actuation will be interpreted as a separately coded language element, e.g. a computer command. Accordingly, so long as the user delays, for example, no more than a second between switch actuations, the user can successfully generate a multi-switch actuation sequence representing a command. Conversely, if the user wishes to generate a succession of one- or two-switch actuation sequences representing plural, sequential commands, then the user must intentionally impose a delay of greater than one second between successive switch actuations.

With practice, such is similar to, and believed to be no more difficult than, properly keying a telegraph with Morse code. Importantly, the invented plural ordered switch selection coding scheme is much more versatile than the Morse coding scheme, and greatly expands the number of codes that quickly, accurately and repeatably can be generated by the user. It will be appreciated that, with three tongue-actuable photosensitive switches 26, 28, 30 in mouthpiece 12, $3^3 + 3^2 + 3 = 27 + 9 + 3 = 39$ different codes can be generated, which will accommodate most English- and foreign-language alphabets as well as many additional symbols or control codes. Thus, apparatus 10 made in accordance with the preferred embodiment of the invention would accommodate a large subset of the keys found on a typical computer keypad (e.g. alphanumerics, cursor control, menu selection) in general-purpose applications such as computer programming or operations, or would accommodate an entire symbolic control language (e.g. on/off, right/left, up/-down, forward/reverse) in special-purpose applications such as semi-automatic machine, elevator or wheelchair control. Of course, computer 18 itself might be used as a controller of another device, system or facility.

Timer circuit 76 preferably is interconnected as shown in FIG. 7 to enforce the above-described inter-switch actuation timing protocol. The output of NAND gate 74, which clocks switch actuation information into shift registers 68, 72, is inverted by an inverter 82 to produce a trigger signal to timer circuit 76. The variable (up to approximately one-second (1−s)) time delay imposed by timer circuit 76 is determined by a 2.2-μF capacitor C21; a 10-kΩ (transistor Q9 base-drive) resistor R29, a 2.2-kΩ pull-up resistor R29, a pull-up resistor R30; and a 1-MΩ variable resistor (potentiometer) R31. It will be understood that transistor Q9 resets timer circuit 76 upon the arrival of a subsequent tone within the user-selectable time delay imposed thereby. Thus, the variable delay produced by timer circuit 76 establishes the delay threshold that determines whether successive switch actuations are interpreted as singular-or plural-switch actuation codes.

Timer circuit 78 is used to produce an enable pulse of proper width (approximately 1-ms in accordance with the preferred embodiment) to command or control decode logic presently to be described. The width of the enable pulse is determined by a 0.1-μF capacitor C22; a 2.2-kΩ pull-up resistor R32; and a 10-kΩ resistor R33. The enable pulse output of timer circuit 78 is inverted by an inverter 84 to produce a (low-) active enable pulse that, while active, enables the outputs of shift registers 68, 72 into a first-tier (address) select-/latch circuit 86, which as may be seen is used as a 1-of-8 decode/latch. The outputs of select/latch circuit 86 will be understood by those skilled in the art to follow the states of the inputs thereof (until the arrival of the trailing edge of the enable signal), thus feeding the inputs through first-tier select/latch circuit 86 to become stable inputs to second-tier (address) select/latch circuits 88, 90, 92, 94, 96, 98, which as may be seen also are used as 1-of-8 decoder/latches. (Each of the illustrated select/latch circuits are National Semiconductor's MM74HC137 "3-8 Line Decoder With Address Latches", with logic inputs thereto (left side in FIG. 7), from top to bottom, including enables G1, G2 ; selects A, B, C; and enable GL , and with logic outputs therefrom (right side in FIG. 7), from top to bottom, including data outputs Y7 , Y6 , Y5 , Y4 , Y3 , Y2 , Y1 , Y0 (where represents a low-active input or output).)

Timer circuit 80 triggers on the trailing edge of the output of timer circuit 78 (corresponding to the trailing, or latching, edge of the enable pulse) to produce a reset signal to shift registers 68, 72, as shown. This ensures that the coded data inputs to second-tier select/latch circuits 88, 90, 92, 94, 96, 98 are latched before shift registers 68, 72 are reset (cleared). In accordance with the preferred embodiment of the invention, timer circuit 80 produces a reset signal of suitable duration, as determined by a 0.1-μF capacitor C24, a 2.2-kΩ pull-up resistor R34 and a 10-kΩ resistor R35. Thus, timer circuits 78, 80 cooperate to provide the needed sequential switch closure data setup time for the decode/latch inputs from the shift registers.

As illustrated in FIG. 7, first- and second-tier select-/latch circuits 86, 88, 90, 92, 94, 96, 98 are interconnected to decode sequential 500-Hz, 700-Hz and 900-Hz signal inputs to receiver 16 into one of thirty-three discrete outputs, which are indicated by labeled arrows. The labeled outputs indicate only thirty-three of the thirty-nine possible coded sequences in which three switches 26, 28, 30 can be actuated. This is simply a simplicity and cost expedient used in the preferred embodiment of the invention: those of skill will appreciate that all thirty-nine (or more, with more than three photosensitive switches and associated encoding/decoding circuitry) coded sequences straightforwardly might be implemented by any suitable sequential and combinational coding and decoding techniques. The labels will be understood to indicate, from left to right and separated by hyphens, the sequential actuations of one or more of left switch 26 ("L), middle switch 28 ("M") and right switch 30 ("R"). It will be understood that left, middle and right switch locations are merely illustrative, and that any desired correspondence with the actual physical locations of plural photosensitive switches within mouthpiece 12 is possible.

Those skilled in the art will appreciate that the labeled outputs of decode/latch circuits 88, 90, 92, 94, 96, 98 represent stable digital signals representing the on/-off states of thirty-three control or command points within a device such as computer 18. It will be understood that, depending upon the device to be orally controlled, these signals straightforwardly would be routed to various control locations such as the key or mouse inputs of a computer terminal; the relays or solenoids of electromechanical or pneumatic equipment; the servo motors of a robotic factory automation machine; etc. Myriad wired or wireless, visible or invisible, silent or audible, proximate or remote, uncoded or uncoded oral control applications present themselves.

Figure 3:
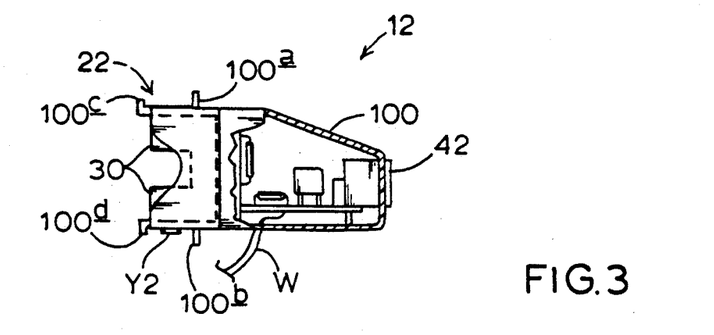
FIG. 3 is a side elevation of the mouthpiece shown in FIG. 2.
Figure 4:
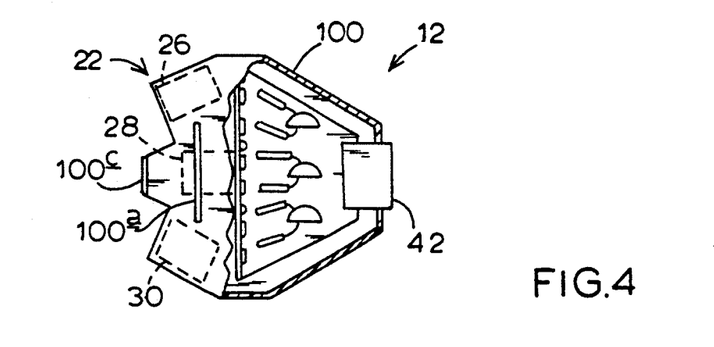
FIG. 4 is a top plan view of the mouthpiece corresponding to FIGS. 2 and 3.
Figure 5:
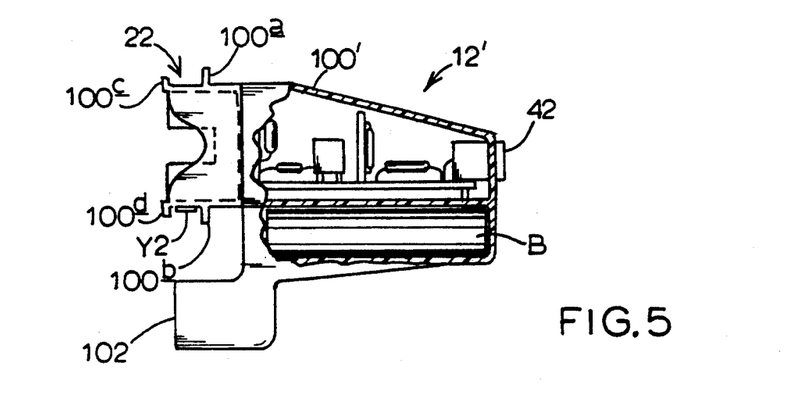
FIG. 5 is a side elevation of a mouthpiece corresponding to that of FIGS. 2 through 4, except that it represents a proposed modification to the preferred embodiment of the invention.

Referring finally to FIGS. 2 through 5, alternative physical embodiments of mouthpiece 12 are described in some detail. It will be understood that the circuitry shown in cutaway view in FIGS. 3 through 5 is illustrative only, and does not represent any particular or preferred physical location or orientation of components or circuit boards. As will be described by contrast between FIGS. 2 through 4, and 5, the desirably lightweight structure of mouthpiece 12 affects the partitioning of transmitter circuitry (FIG. 6) between mouthpiece 12 and transmitter 14 (FIG. 1). Those of skill in the arts will appreciate that all of transducer electronics 32 might be integrated into a very large-scale integration (VLSI) semiconductor chip that, along with a button-type watch or camera battery, readily can be fitted within mouthpiece 12, thereby obviating what is seen in FIG. 1 to be a separate transmitter 14 electronics housing.

FIG. 2 is a rear elevation, i.e. a user's eye view, of mouthpiece 12 made in accordance with the preferred embodiment of the invention. Mouthpiece 12 includes a lightweight but durable rigid housing 100 that is shaped and sized comfortably with intraoral structure 22 extending rearwardly within the mouth. Slotted, photosensitive switches 26, 28, 30 are positioned in spaced relation generally in an circular arc (refer briefly to FIG. 4) within a rear recessed region of housing 100 so that their slots are aligned in a generally horizontal plane. Each of the illustrated slotted switches may be of any suitable design to produce a device of compact size that readily can be actuated by extending the tip of the tongue into a slot or aperture to interrupt a beam of light. Housing 100 is provided on its generally planar top surface with an upwardly extending circular tab 100a, and on its generally planar bottom surface with a downwardly extending circular tab 100b. Housing 100 also is provided on its generally planar top surface with an upwardly extending rectangular tab 100c, and on its generally planar bottom surface with a downwardly extending rectangular tab 100d.

Turning to FIG. 3, it may be seen that tabs 100a, 100b are spaced forward of the rear edge of housing 100 which is defined by tabs 100c, 100d. The spaces provided between upper tabs 100a, 100c and between lower tabs 100b, 100d are for the user's upper and lower teeth, respectively. The tabs make it possible for the user by positioning both teeth and lips therebetween and therearound firmly to hold mouthpiece 12 in the mouth in such portion that the tip of the tongue easily can be extended within a selected slot of any of slotted photosensitive switches 26, 28, 30. FIG. 3 also fragmentarily shows plural conductor cable or wire harness W extending from housing 100 for electrical connection with the electronics housed within transmitter 14. It may be seen from FIG. 3 that the location of laterally aligned contacts Y1, Y2 of normally open switch 24 is such that the user's lower lip will bridge the contacts when mouthpiece 12 is positioned properly relative to the user's mouth.

Brief reference to FIG. 4 illustrates the circularly arcuate spacing of photosensitive switches 26, 28, 30 (shown in dashed lines) and the generally mouth-conforming shape of intraoral structure 22. Importantly, intraoral structure 22 intrudes only marginally into the user's mouth, rendering swallowing and lingual placement easier and more natural. As is suggested by FIG. 4, in accordance with the preferred embodiment of the invention, housing 100 of mouthpiece 12 contains only a portion of transducer electronics 32 (suitably mounted, in accordance with conventional techniques, on one or more PCBs, as indicated) the remainder of which is contained in a separate housing with the majority of the electronics associated with transmitter 14. The advantage of thus partitioning the circuitry is that mouthpiece 12 is extremely lightweight, and imposes little or no discernible burden on the user.

Preferably, the weightier components of transmitter 14, especially the battery or batteries, are not physically contained within housing 100 of mouthpiece 12, but are connected to the remaining electrical circuitry by plural conductor cable or wire harness W. I.e. in accordance with the preferred embodiment, most of mouth-placement detection circuit 34 (except, of course, for contacts Y1, Y2 of switch 24), oscillator circuit 36, and modulator 38 are housed in transmitter 14, whereas photosensitive switches 26, 28, 30 and associated circuitry along with output driver circuit 42 are housed in mouthpiece 12. With this preferred partitioning, primarily only those components that need to be part of mouthpiece 12, e.g. the photosensitive switches that must be lingually controlled and the driver circuit that may need to be pointed toward a remotely controllable device, are included in housing 12 and the rest of the circuitry including the relatively heavy battery are included in a separate housing conveniently worn on the user's body, e.g. on a strap extending around the neck as shown in FIG. 1.

Turning finally to FIG. 5, a proposed alternative embodiment of the invention is shown in which a mouthpiece 12' includes a housing 100' that is sufficiently large to contain the lingual transducer and all of the associated transducer and transmitter electronics, including battery or batteries B. In accordance with this embodiment, in order to relieve the user from the added weight of mouthpiece 2', housing 100' is equipped with a chin-confronting structure 102 for countering the tendency of the cantilever structure otherwise to rotate (clockwise, in FIG. 5) and to cause uncomfortable pressure on the user's lips and teeth.

A preferred method of the invention corresponding to the preferred embodiment now may be seen to involve detecting the (not-necessarily-contacting) proximity of a user's tongue to one or more intraoral sensors (such as by photosensitive switches 26, 28, 30, driven by oscillator 36, selectively switching on Q3, Q4 or Q5, preferably in a predetermined, plural switch actuation sequence), interpreting said proximity detecting as one or more lingual control codes (such as by shift registers 68, 72, controlled by timer circuits 76, 78, 80 to drive select/latch circuits 86, 88, 90, 92, 94, 96, 98) and utilizing said codes as commands for controlling a device that may be remote from the user (such as computer 18). Such invented method may be seen not necessarily to include intermediate transmitting or receiving steps (involving modulator 38, driver 42, antenna 46, receiver/demodulator circuit 48, decode/timer circuits 50/56, 52/58, 54/60 and associated NAND and inversion gating circuitry), yet it enables users, who may have only limited use of their hands, adroitly to control and operate simple or sophisticated equipment.

Accordingly, while the invention has been shown and described with reference to a preferred embodiment and method, it will be understood by those skilled in the art that changes might be made thereto without departing from the spirit of the invention, yet while achieving many of the advantages of the invention.

It is claimed and desired to secure by Letters Patent:

1. A method of orally controlling a device through selective placement of the tongue, comprising the following steps:
   selectively placing the tongue in the aperture of one of a plurality of intraoral sensors positioned at predetermined locations in the mouth to cause a change of state in the output of said sensor;
   selectively placing the tongue in the same or another selected sensor to cause a change of state in the output of the sensor selected; and
   detecting and interpreting the outputs of said plurality of sensors in accordance with a coding scheme to produce commands for controlling a device that may be remote from the user.

2. The method as in claim 1 in which said step of placing the tongue in the aperture of an intraoral sensor includes interrupting a light beam to open a photosensitive switch.

3. The method as in claim 1 in which said step of placing the tongue includes selectively placing the tongue in one or another of three predetermined locations in the mouth, each said location being the location of the aperture of one of three intraoral sensors positioned in the mouth.

4. An oral controller comprising:

a mouthpiece including a plurality of intraoral sensors, each sensor including an aperture for receiving the tip of the user's tongue therein to cause the sensor to output a signal;

a transmitter operatively coupled with said sensors for generating a signal stream indicative of the sequential activation of selected sensors by the user for transmission to a remote receiver; and a receiver responsive to said signal stream, said receiver decoding said signal stream into one or more coded symbols for controlling a device remote from the user based upon the user's selective operation of said mouthpiece sensors in accordance with a predetermined language.

5. The controller of claim 4, wherein said transmitter generates a signal stream that is audible to the user, thereby providing aural feedback aiding accurate tongue placement.

6. An oral controller comprising:

a mouthpiece including an intraoral region having plural normally closed switches operable by the selective placement of a user's tongue proximate thereto;

a mouth-placement detection circuit coupled with said mouthpiece for applying power to said switches upon detection that said mouthpiece is in contact with the user's mouth;

a transmitter operatively coupled with said switches, said transmitter detecting the opening of each of said switches and generating a signal stream indicative thereof for transmission to a remote receiver; and a receiver responsive to said signal stream, said receiver decoding said signal stream into one or more coded symbols for controlling a device remote from the user based upon the user's selective operation of said switches in accordance with a predetermined language.

7. The controller of claim 6, wherein said switches are photosensitive and are energized periodically at a predefined low duty cycle to preserve power.

8. A lingual transducer comprising:

an intraoral structure including a normally open switch that is closed when said structure is placed is placed in a user's mouth, said structure further including at least one photosensitive switch the coupleable terminals of which are supplied with a voltage upon closure of said normally open switch, sad photosensitive switch thereafter being normally closed by a light beam and being actuable by lingual placement in the path of said beam momentarily to interrupt the same and to open said photosensitive switch, and electronics coupleable with sad structure for detecting such closure of sad normally open switch, supplying thereupon such voltage to said photosensitive switch, detecting such actuation of said photosensitive switch and generating a signal indicative of such lingual placement in the path of said beam.

9. The transducer of claim 8, wherein said intraoral structure includes plural photosensitive switches, further comprising a transmitter operatively coupled with said photosensitive switches, said transmitter detecting openings of said switches and generating a coded signal indicative thereof.

10. The transducer of claim 9, wherein said coded signal is a modulated infrared carrier.

11. The transducer of claim 8, wherein said signal is audible to the user, thereby providing aural feedback aiding accurate lingual placement.

* * * * *